United States Patent [19]

Andrulis, Jr.

[11] Patent Number: 5,405,855
[45] Date of Patent: Apr. 11, 1995

[54] TREATMENT OF INSULIN RESISTANT DIABETES WITH THALIDOMINE

[75] Inventor: Peter J. Andrulis, Jr., Bethesda, Md.

[73] Assignee: Andrulis Pharmaceuticals Corp., Beltsville, Md.

[21] Appl. No.: 172,154

[22] Filed: Dec. 23, 1993

[51] Int. Cl.⁶ .......................................... A61K 31/445
[52] U.S. Cl. ................................... 514/323; 514/866
[58] Field of Search ............... 514/339, 343, 323, 866

[56] References Cited

U.S. PATENT DOCUMENTS 5,104,899  4/1992  Young et al. .................. 514/646

Primary Examiner—Raymond Henley, III
Assistant Examiner—T. J. Criares
Attorney, Agent, or Firm—Isaac A. Angres

[57] ABSTRACT

A method for treating insulin-resistant diabetes in mammals which comprises administering to said afflicted animals a prophylactically or therapeutically effective amount of thalidomide.

3 Claims, No Drawings

TREATMENT OF INSULIN RESISTANT DIABETES WITH THALIDOMINE

The present invention relates to a novel method for treating insulin-resistant diabetes in obese animals with a therapeutically effective amount of thalidomide.

DESCRIPTION OF THE PRIOR ART

The disease diabetes mellitus is characterized by metabolic defects in the production and utilization of glucose which result in the failure to maintain appropriate blood sugar levels. The result of this defect is elevated blood glucose or hyperglycemia. Research on the treatment of diabetes has centered on attempts to normalize fasting and postpromdial blood glucose levels. Treatments have included parenteral administration of exogenous insulin, oral administration of drugs, and dietary therapies.

Initially it was thought that hyperglycemia was simply the result of a deficiency in the supply of insulin, the key hormone which controls glucose metabolism. As a result, research focused on the source of insulin production, the beta cells of the pancreas, and pharmaceutical agents were discovered which stimulated the production of insulin by the pancreas. Although it remains true that a deficiency of insulin does cause hyperglycemia, it has now been recognized that other metabolic defects can be a major cause of elevated blood glucose.

In 1979, the World Health Organization officially characterized diabetes into three types (1) Non-insulin dependent diabetes (NIDDM); (2) Insulin-dependent diabetes (IDDM); and (3) Gestational diabetes mellitus.

By 1990, 20 million people world wide were diagnosed as insulin-dependent diabetics and were being treated with insulin. In the U.S., one million people are diagnosed with IDDM and 13 million with NIDDM.

Classic symptoms in adults are polyuria, polydipsia, ketonuria, rapid weight loss together with elevated levels of plasma glucose. Normal fasting plasma glucose levels is <115 mg/dl. In diabetic patients levels are fund to be >140 mg/dl. In children the symptoms are the same as adults except that in adults diabetes can be diagnosed if the fasting glucose tolerance test levels are above e normal, while as in children both levels of fasting glucose tolerance as well as oral glucose tolerance test levels have to be above normal on more than one accession (*Diabetes*, 1979, 28:1029-57).

As early as 1875 Bouchardat had noted that overweight individuals with glucosuria became aglucosuria after weight loss from fasting and low caloric diets. This was used as the only effective therapy until 1922. In 1923, insulin was discovered a possible treatment for those who were dying of ketoacidosis.

Since insulin is administered as an injection, there has always been an ongoing search for an oral form of treatment for diabetes. In 1957 oral sulfonylurea and biguanidine therapy was being used, but due to the fatal side effects, especially of phenformin, FDA stopped the marketing of these drugs in the U.S. However, the drugs are still available outside the U.S. The mechanism of action of sulfonylurea drugs is to stimulate the pancreatic B cells, which are res[responsible for the secretion of insulin. The precise cellular and biochemical events that are responsible for the stimulatory action are not known. There is limited information regarding their pharmacokinetics and bioavailability after oral administration. The adverse effects of sulfonylurea treatments is that the sulfonylurea metabolites are excreted by tubular secretion in the kidneys which is contraindicated for patients with liver or renal disease.

The mechanism of action of biguanides is thought to be the inhibition of glucose uptake by peripheral tissues by inhibiting glucose oxidation. Insulin dependent diabetes mellitus (IDDM) is an autoimmune disease in which the pancreatic islets are infiltrated by mononuclear leukocytes (insulitis) and the insulin-producing islet b-cells are selectively destroyed (Palchak et al., *Immunol. Immunopathol.* 1992, 65:129-34). This study found that suppression of TNF production may be causally related to IDDM. A long asymptomatic period of B-cell autoimmunity during which insulin secretory capacity is progressively lost usually precedes the onset of IDDM (Eisenbarth et al., *Diabetes*, 1993, 42:941-7). However, one study (Procellati et al., *Diabetes*. 1993, 42:1055-64) showed that therapeutic subcutaneous doses of insulin activates the sympathetic nervous system which can be measured by elevated plasma norepinephrine concentrations. Secondly, therapeutic hyperinsulinemia blunts the basoconstrictive response to activation of the sympathetic nervous system. This is a possible explanation why some IDDM patients develop neuropathy.

In the case of NIDDM patients, a further look is being taken to understand the connection between obesity and diabetes. Several studies are underway to find the molecular mechanism involved in the disease.

Most NIDDM patients tend to be obese. Obesity which is the result of an imbalance between caloric intake and energy expenditure is highly correlated with insulin resistance and diabetes (Hotamisligil, Spiegelman et al., *Science*, 1993, 259:87-91). However, the molecular mechanisms that are involved in obesity-diabetes syndrome are not clear. Studies have shown that obesity impairs insulin sensitivity. There is some relationship between obesity and insulin action which affects insulin suppression of hepatic glucose production and stimulation of glucose disposal of peripheral tissues. Insulin has been found to be a potent inhibitor of lipolysis.

Although the role of abnormalities of fat metabolites in the pathogenesis of obese diabetics state is unclear, a search for an appropriate oral medication for diabetes has focused researchers in trying to understand the function of adipose tissue which is a major site for energy storage and mobilization. Adipose tissue is found around the heart, kidney and pancreas. Water content is low (5–15%) compared to most other lean organs (70–72%). These adipose-layered organs are made up of adipocytes which store triglyceride lipids with high caloric density. (For example, 1 kg of fat contains 7,700 Kcal of triglycerides while one kg of muscle contains 1,200 kcal of glycogen and protein.) Hormonal stimulation of adipocyte metabolites process is regulated by lipogenic hormones, such as insulin and lipolytic hormones. Insulin regulates glucose transport from the intracellular microsomal location to the plasma membrane prompting glucose metabolism by enzyme activation and protein synthesis.

Cytokines are small antigen-nonspecific glycoproteins (10–30 kDa) that are synthesized and rapidly secreted by a variety of different cells in response to numerous stimuli (Corbett et al., *Diabetes*, 1992, 41:897-903). The specific cytokine required to induce B-cell dysfunction and destruction depend on the species being studied. IL-1 alone appears to be sufficient to induce B-cell dysfunction and destruction in the rat. Paradoxically, in vivo injections of IL-1 also produce antidiabetogenic effects in the NOD mouse. The mechanism by which these cytokines produce such variable effects is unknown. Corbett proposes that the antidiabetogenic effects observed with in vivo administration of this cytokine may be the result of macrophage-mediated nitric oxide formation.

The mechanism of cytokine action on the B-cells are unknown. However, nitric oxide, resulting from cytokine-induced expression of nitric oxide synthase has been implicated as the cellular effector molecule mediating B-cell dysfunction (Corbett et al., *Diabetes*, 1992, 41:897-903).

A main characteristics displayed by diabetic obese animals is insulin resistance or insulin insensitivity. Insulin resistance is a condition in which available insulin, secreted by the pancreas and circulating in the bloodstream, fails to stimulate sufficient glucose uptake and utilization in insulin-sensitive tissue. This inability of certain tissues including liver, muscle, and fat, whose metabolic machinery is normally sensitive to insulin, to utilize glucose efficiently or to control endogenous glucose synthesis and glycogenolysis, results in elevated blood glucose.

Compounds which stimulate and/or potentiate the biological action of insulin would be beneficial in the treatment of hyperglycemia resulting from mild to moderate insulin insufficiency or insulin insensitivity. A compound which would stimulate or mimic insulin's action would correct beta insulin deficiency and insulin resistance by its own insulin-like action. Further, a compound which would potentiate insulin's action would ameliorate insulin deficiency by rendering the small amount of insulin which is present more efficacious and would decrease insulin resistance directly by acting to make insulin more effective. Their compounds which would show insulin-like and/or insulin potentiating activity would be beneficial for the treatment of diabetes.

The thalidomide of the present invention, stimulates and potentiates the biological action of insulin. It stimulates insulin's action at least in part by promoting the cellular uptake and metabolism of glucose in the absence of insulin. It potentiates insulin's action by exerting actions in the presence sub-maximal concentrations of insulin. The exact mechanism by which the compound thalidomide acts to produce the observed effects is not known and the invention should not be limited to any particular mechanism of action. Nonetheless, the prior art is silent regarding the treatment of insulin-resistant diabetes in obese animals with thalidomide.

SUMMARY OF THE INVENTION

The present invention is a method for treating insulin-resistant diabetes in obese animals with a therapeutically effective amount of thalidomide.

The present invention further relates to a therapeutic method for treating insulin-resistant diabetes in obese animals which comprises administering to said afflicted animals a prophylactically or therapeutically effective amount of thalidomide.

The invention also relates to a method of treating hyperglycemia in a mammal in need of such treatment which comprises administering to said mammal an effective amount of thalidomide.

This invention also relates to a pharmaceutical composition which comprises an effective antidiabetic amount of a thalidomide in association with a pharmaceutically acceptable carrier.

This invention further relates to a pharmaceutical composition which comprises an effective hypoglycemic amount of thalidomide in association with a pharmaceutically acceptable carrier.

DESCRIPTION OF THE PREFERRED EMBODIMENTS

The present invention is a method for treating insulin-resistant diabetes in obese animals which comprises administering to said afflicted animals a prophylactically or therapeutically effective amount to decrease the glucose levels of thalidomide.

The preferred form of administration of thalidomide is by oral administration. When thalidomide is administered orally, it is typically administered in the form of tablets, capsules, dispensable powders, granules or suspensions. The compositions typically may contain 0.5 to 50% of suspending agent, syrups containing for example, from about 10 to 50% sugar, and elixirs containing, for example, from about 20 to 50% ethanol, and the like, or parenterally in the form of sterile injectable solutions or suspensions containing from about 0.5% up to about 5% suspending agent in an isotonic medium. These pharmaceutical preparations may contain, for example, from about 0.5% up to about 90% of the thalidomide as active ingredient in combination with the carrier, more usually between 5% and 60% by weight.

The effective dosage of thalidomide employed may vary depending on the mode of administration and the severity of the condition being treated. However,, in general satisfactory results are obtained when the thalidomide of invention is administered at a daily dosage of from about 5 mg to abut 100 mg per kg of animal body weight, preferably given in divided doses two to four times a day, or in sustained release form. For most large mammals, the total daily dosages from about 30 mg to about 1,000 mg preferably from about 100 milligrams to 500 mg. Dosage frms suitable for internal use comprise from about 100 to 500 mg of the thalidomide inintimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that thalidomide may be administered orally as well as by intravenous, intramuscular, r subcutaneous routes if necessary. Solid carriers include starch, lactose, dicalcium phosphate, microcrystalline cellulose, sucrose and kaolin, while liquid carriers include sterile water, polyethylene glycol, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and anti-oxidants, e.g., vitamin E, ascorbic acid, BHT and BHA.

The preferred pharmaceutical compositions from the stand-point of ease of preparation and administration are solid composition, particularly tablets and hard-filled or liquid-filled capsules. Oral administration of the compounds is preferred Thalidomide may also be administered parenterally or intraperitoneally. Solutions or suspensions of thalidomide can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be solvent or dispersion medium containing, for example, water, ethanol, polyol (e.g., glycerol, propylene glycol and liquid polyethylene glycol), suitable mixtures thereof, and vegetable oils.

Thalidomide is tested for its insulin-like and insulin-potentiating activity according to the following procedure: Male, Wistar strain, Royal Hart rats weighing 125–170 g. were sacrificed by decapitation. Their abdominal cavities were opened and distal or thin portions of epididymal fat pads excised, accumulated, and placed in 0.9% saline. The tissue was weighed and placed at a density of about 0.4 g/ml in Krebs-Henseleit bicarbonate (KHB) buffer containing 5 mg of crude bacterial collagenase per ml. (The KHB is composed of 118 mM sodium chloride; 4.7 mM potassium chloride; 1.2 mM calcium chloride; 1.2 mM potassium dihydrogen phosphate; 1.2 mM magnesium sulfate heptahydrate; 25 mM sodium bicarbonate and 0.3 mM glucose and is saturated with oxygen:carbon dioxide (95:5).) The tissues were incubated with collagenase for one hour at 37° C. with gentle agitation in a Dubnoff metabolic shaker. At the end of this digestion period the cells were washed five times with twice their volume of KHB buffer containing fatty acid free bovine serum albumin (Pentex Fraction V) at a concentration of 3%. The digest was filtered through two layers of gauze and suspended in KHB buffer with albumin to a volume ten times the initial total weight of the fat pads. Incubation of one ml aliquots of the cell suspension was carried out in 17×100 mm plastic Falcon tubes. Cells were incubated in the presence or absence of test compound and insulin. All tubes contained 0.15 μci D-glucose-U-$^{14}$C (specific activity 200 mM/mmole).

Recrystallized porcine insulin (specific activity—25.5 U/mg) was dissolved in 0.9% saline adjusted to pH 3 with hydrochloric acid. The insulin was added to the cells at a concentration of approximately 5 μU/ml and control or basal cells received comparable volumes of pH 3 saline. Thalidomide is dissolved in 50% dimethylsulfoxide-50% ethanol and added to the cells at a concentration of 100 μg/ml. Control cells received comparable volumes of dimethyl sulfoxide-ethanol.

After the tubes are loaded with insulin and thalidomide or other vehicles, and cell suspension, they are capped with sleeve stoppers fitted with hanging, plastic center wells. Each well contained a small section of folded filter paper. The tubes are then gassed for about one minute with oxygen:carbon dioxide (95:5) via needles inserted through the septum of the stopper.

Immediately after gassing, the radioactive glucose is injected into the incubated and the tubes are placed in a 37° C. metabolic shaking water bath and were incubated for one hour with gentle agitation.

At the end of the incubation, 0.4 ml of Hyamine hydroxide and then 0.5 ml of 5N sulfuric acid are carefully injected into the center well and cell suspension, respectively. The acidified cell suspension is then incubated an additional 30 minutes at room temperature with gentle agitation. At the end of this carbon dioxide collection period, the center wells are drop into vials containing 10 ml of Dimiscint ® scintillation cocktail and the radioactivity counted by liquid scintillation spectrometry.

The measurement of carbon dioxide radioactivity in counts per minute which is produced by these cells in the absence of both test compound and insulin is the basal level (b). Radioactivity produced in the presence of thalidomide only, insulin only and both test compound and insulin are (c), (i) and (ci), respectively. Each of (c), (i) and (ci) is then expressed as a percent of the basal value: $C=(c/b)$; $I=(i/b)$; $CI=(ci/b)$. Finally, insulin-like activity (%C/I) is calculated using the formula $$\%C/I = \frac{(100)(C-100)}{(I-100)};$$

and insulin-potentiating activity (%P) is calculated using the formula $$\%P = \frac{(100)(CI-C-I+100)}{(I-100)}.$$

The testing indicates insulin-like activity for thalidomide. In making the pharmaceutical compositions, thalidomide will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methylcellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions may be formulated so as to provide rapid, sustained or delayed release of the active ingredient after administration to the patient by employing procedures well-known in the art.

The invention will be more fully described in conjunction with the following specific examples which are not to be construed as limiting the scope of the invention.

Example 1

Hard gelatin capsules are prepared using the following ingredients

| | Quantity (mg/capsule) |
|---|---|
| Thalidomide | 250 |
| Starch dried | 200 |
| Magnesium stearate | 10 |

The above ingredients are mixed and filled into hard gelatin capsules in 460 mg quantities

Example 2

A tablet formula is prepared using the ingredients below

| | Quantity (mg/tablet) |
|---|---|
| Thalidomide | 250 |
| Cellulose, microcrystalline | 400 |
| Silicon dioxide, fumed | 10 |
| Stearic acid | 5 |

The components are blended and compressed to form tablets each weighing 665 mg.

Example 3

Tablets each containing 60 mg of active ingredient are made up as follows:

| | |
|---|---|
| Thalidomide | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate nd talc, previously passed through a No. 60 mesh U.S. sieve, are then added to the granules which, after mixing, are compressed by a tablet machine to yield tablets each weighing 150 mg.

Example 4

Capsules each containing 80 mg of medicament are made as follows:

| | |
|---|---|
| Thalidomide | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No./45 mesh U.S. sieve, and filled into hard gelatin capsules in 200 mg quantities.

Example 5

Suspensions each containing 50 mg of medicament per 5 ml dose are made as follows:

| | |
|---|---|
| Thalidomide | 50 mg |
| Sodium carboxymethylcellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Example 6

Capsules each containing 150 mg of medicament are made as follows:

| | |
|---|---|
| Thalidomide | 150 mg |
| Starch | 164 mg |
| Microcrystalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.

It is to be understood that the forms of the invention herein are to be taken as preferred examples of the same, and that various changes may be made without departing from the spirit of the invention or scope of the subjoined claims.

What is claimed is:

1. A method for treating insulin-resistant diabetes in mammals which comprises administering to said afflicted mammals a therapeutically effective amount of thalidomide.

2. The method of claim 1 wherein said effective amount is in the range of 5 milligrams to 100 milligrams per kilogram of body weight.

3. The method of claim 1 wherein the thalidomide is administered with a pharmaceutically acceptable carrier.

* * * * *